(12) United States Patent
Amundsen et al.

(10) Patent No.: US 8,966,979 B2
(45) Date of Patent: Mar. 3, 2015

(54) METHOD AND DEVICE FOR MEASURING THE THICKNESS OF ANY DEPOSIT OF MATERIAL ON AN INNER WALL OF A STRUCTURE

(75) Inventors: Lene Amundsen, Porsgrunn (NO); Rainer Hoffmann, Skien (NO)

(73) Assignee: Statoil Petroleum AS, Stavanger (NO)

( * ) Notice: Subject to any disclaimer, the term of this patent is extended or adjusted under 35 U.S.C. 154(b) by 559 days.

(21) Appl. No.: 13/146,950

(22) PCT Filed: Jan. 15, 2010

(86) PCT No.: PCT/EP2010/050464
§ 371 (c)(1),
(2), (4) Date: Aug. 31, 2011

(87) PCT Pub. No.: WO2010/086238
PCT Pub. Date: Aug. 5, 2010

(65) Prior Publication Data
US 2011/0303012 A1 Dec. 15, 2011

(30) Foreign Application Priority Data
Jan. 30, 2009 (NO) .................................. 20090483

(51) Int. Cl.
*G01B 7/06* (2006.01)
*G01H 13/00* (2006.01)
*G01N 29/12* (2006.01)

(52) U.S. Cl.
CPC ................ *G01B 7/066* (2013.01); *G01N 29/12* (2013.01); *G01H 13/00* (2013.01)
USPC ................ 73/579; 73/591; 73/40.5 A; 73/592

(58) Field of Classification Search
USPC ............................... 73/579, 591, 592, 40.5 A
See application file for complete search history.

(56) References Cited

U.S. PATENT DOCUMENTS

| | | | |
|---|---|---|---|
| 4,817,430 A | 4/1989 | Benes et al. | |
| 5,661,248 A | 8/1997 | Bernicot et al. | |
| 5,756,898 A | 5/1998 | Diatschenko et al. | |
| 6,286,370 B1 * | 9/2001 | Sinha | 73/579 |
| 7,430,914 B2 * | 10/2008 | Mitchell et al. | 73/649 |

(Continued)

FOREIGN PATENT DOCUMENTS

FR 2754898 A1 4/1998
JP 1-112134 A 4/1989

(Continued)

OTHER PUBLICATIONS

Edmonds et al., "Simulating Wax Deposition in Pipelines for Flow Assurance", Energy & Fuels, vol. 22, No. 2, 2008, XP009131249, pp. 729-741.

*Primary Examiner* — Lisa Caputo
*Assistant Examiner* — Rose M Miller
(74) *Attorney, Agent, or Firm* — Birch, Stewart, Kolasch & Birch, LLP (57) ABSTRACT

A method of measuring the thickness of any deposit of material (28) on an inner wall (12) of a structure (14). The method comprises: (a) causing vibrations in the structure; (b) detecting said vibrations in the structure; (c) determining a resonance frequency of the structure based on the detected vibrations; and (d) determining the thickness of any deposit of material on the inner wall of the structure based on the determined resonance frequency.

19 Claims, 5 Drawing Sheets

10: Measurement device
18: Device
20: Sensor
24: First determiner
26: Second determiner
30: Unit

(56) References Cited

U.S. PATENT DOCUMENTS

2003/0033870 A1* 2/2003 Shah et al. ............... 73/299
2007/0095153 A1* 5/2007 Rieder et al. ............ 73/861.356

FOREIGN PATENT DOCUMENTS

| WO | WO 2005/010522 A2 | 2/2005 |
| WO | WO 2008/103176 A1 | 8/2008 |

* cited by examiner

Fig. 1

10: Measurement device
18: Device
20: Sensor
24: First determiner
26: Second determiner
30: Unit

10: Measurement device
20: Sensor
24: First determiner
26: Second determiner
30: Unit

METHOD AND DEVICE FOR MEASURING THE THICKNESS OF ANY DEPOSIT OF MATERIAL ON AN INNER WALL OF A STRUCTURE

FIELD OF THE INVENTION

The present invention relates to a method of measuring the thickness of any deposit of material on an inner wall of a structure, for instance an oil pipeline. The present invention also relates to a corresponding device or system.

BACKGROUND OF THE INVENTION

Wax deposition at the inner wall of oil pipelines is a severe problem in today's oil production infrastructure. When warm oil flows through a pipeline with cold walls, wax will precipitate and adhere to the walls. This in turn will reduce the pipeline's cross-sectional area, which without counter measures will lead to a loss of pressure and ultimately to a complete blockage of the pipeline.

To know when remediation techniques (e.g. pigging, heating, etc.) have to be applied, it is essential to know the current thickness of the wax layer. Known techniques for determining or measuring the current wax layer's thickness include the use of pipeline inspection gauges (pigs), pressure pulse techniques, and pressure drop measurement (over the complete pipeline). However, each of these known techniques has several drawbacks. For instance, pigs and pressure pulse techniques give no continuous measurement, they may disturb operation procedures, and they are expensive. A pressure drop measurement approach gives only an integral measurement over the whole pipe length, and the measured pressure drop is influenced by a number of parameters in addition to wax thickness (e.g. the roughness of the inside of the pipeline), so there is really no direct correlation to wax thickness.

SUMMARY OF THE INVENTION

It is an object of the present invention to at least partly overcome the above problems, and to provide an improved deposit thickness measurement method.

This object, and other objects that will be apparent from the following description, is achieved by a method and device according to the appended independent claims. Advantageous embodiments are set forth in the appended dependent claims.

According to an aspect of the present invention, there is provided a method of measuring the thickness of a deposit of material on an inner wall of a structure, the method comprising:
 (a) heating a portion of the structure;
 (b) detecting vibrations at the heated portion;
 (c) detecting vibrations at an unheated portion of the structure;
 (d) determining a resonance frequency or frequencies of the structure based on the vibrations detected at (c); and
 (e) determining the thickness of a deposit of material on the inner wall of the structure at said unheated portion using the determined resonance frequency or frequencies, this step using the vibrations detected at (b) as calibration data.

A resonance or resonant frequency means here the lowest characteristic frequency of the structure and/or any of its overtones or harmonics. The lowest characteristic frequency of the structure may also be referred to as the eigen frequency of the system. The resonance frequency may also be approximately equal to the natural frequency of the structure.

The present invention is based on the understanding that the resonance frequency of the structure will change as soon as for instance a wax layer starts forming on the inside of the structure. This change in resonance frequency is due to the changed total elasticity coefficient (vibration damping because of the viscous-elastic wax layer). Thus, measured resonance frequency can be correlated to wax layer thickness. The present method advantageously provides for low-cost, continuous wax thickness measurement, which in turn allows wax remediation techniques to be applied (just) in time.

The vibrations in the structure may for instance be caused by means of a device adapted to give a mechanical impulse to the structure, e.g. like a hammer hitting the structure. Alternatively, the vibrations in the structure may be caused by means of a medium flowing inside structure. E.g. an irregular two-phase slug flow may exchange mechanical energy with the structure, setting the structure into vibration. Also, the vibrations in the structure may be caused by changing the flow rate of a medium flowing inside the structure, in case the flow is not irregular enough.

Further, the vibrations in the structure may be detected by means of a sensor mechanically connected to the structure, and also to a fixed (reference) point, for measuring the distance variation between the structure and the fixed point. Alternatively, the vibrations in the structure may be detected by means an optical detector. In this way, no mechanical contact is necessary. As another alternative, an accelerometer fixed to the outside of the structure may be used.

In one embodiment, the resonance frequency used to determine the thickness of any deposit of material on the inner wall of the structure is the lowest characteristic frequency of the structure. This will give the highest accuracy.

In one embodiment, the method further comprises (e) predicting the thickness of any deposit of material at one or more portions of the structure remote from where the vibrations are detected using a material deposition model of the structure. Hence, even though the present method basically provides a point measurement, accurate prediction of the deposition thickness at other portions or parts of the structure may beneficially be provided.

In one embodiment, the method further comprises performing the steps (a)-(d) for different portions of the structure, e.g. at several locations along the structure. Except for giving information about the exact deposition thickness at said locations, the information may beneficially be used to update in real-time the above mention material deposition model, to increase the accuracy of the model output.

In one embodiment, a resonance frequency of the structure is determined by determining the frequency at which the structure vibrates at a maximum amplitude.

In one embodiment, the thickness of any deposit of material on the inner wall of the structure is determined by comparing the (currently) determined resonance frequency with a previously determined resonance frequency of the structure, for which previously determined resonance frequency the thickness of any deposit of material on the inner wall of the structure is known. The previous resonance frequency may for instance be determined for a clean structure.

In one embodiment, said structure is a pipeline, for instance an oil pipeline.

In one embodiment, said material is wax. Wax may refer to solids that precipitate from fluids due to thermodynamically changes. These solids include solids typically dissolved in crude oil at well bore conditions such as asphaltenes, higher paraffins, hydrates, and inorganic and organic salts. The composition of the wax will depend on the origin of the fluid stream.

In a structure like a pipe, the heating should keep the inner pipe wall above deposit appearance temperature, thus preventing deposition in the heated portion. The heating may for instance be achieved by electrical heating cables installed locally around the pipe. An advantage of this embodiment is that the determination of the resonance frequency may be more accurate, since unwanted vibrations caused by the pipe flow, especially multiphase pipe flow with flow patterns like wavy flow or slug flow, exerting significant dynamic forces on the pipe wall may be accounted for. This however does not deny that the internal flow indeed may be used as a source for causing vibrations, as appreciated by the skilled person.

The steps performed in respect of the heated and unheated portions of the structure may be carried out using respective different measurement devices, such that the calibration may be carried out in real time, which increases the accuracy of the measurement.

The present method may further comprise determining at least one of: (i) the amount of damping of the vibrations at the resonance frequency, i.e. how the amplitude of the resonance frequency decreases over time; (ii) the shift of the frequencies of the harmonics of the structure; and (iii) the amount of damping of the vibrations at the harmonics of the structure, based on the detected vibrations. Data resulting from at least one of (i)-(iii) may then be used to determine the elasticity modulus (both the real and the imaginary component) of any deposit of material on the inner wall of the structure. For instance, the amount of damping for each harmonic frequency will differ depending on the elasticity modulus. Determining the elasticity modulus of the deposit of material on the inner wall of the structure is beneficial in that it allows establishing what kind of material the deposit is made of.

According to a second aspect of the present invention there is provided a method of determining the stiffness of a material deposited on an inner wall of a structure, the method comprising:
  detecting vibrations in the structure;
  determining a resonance frequency or frequencies of the structure based upon
  the detected vibrations; and
  determining a stiffness of a deposited material by observing changes in the resonance frequency/frequencies or resonance amplitude/s over time According to a third aspect of the present invention there is provided apparatus for measuring the thickness of a deposit of material on the an inner wall of a structure, the apparatus comprising:
  a sensor placeable on the outside of the structure for detecting vibrations in the structure;
  a signal processor for determining a resonance frequency of the structure based on the vibrations detected by the sensor means; and
  an analyser for determining the thickness of a deposit of material on the inner wall of the structure based on the resonance frequency determined by said signal processor.

According to a fourth aspect of the present invention there is provided apparatus for determining the stiffness of a material deposited on an inner wall of a structure, the apparatus comprising:
  a sensor for detecting vibrations in the structure;
  a signal processor for determining a resonance frequency or frequencies of the structure based upon the detected vibrations; and
  an analyser for determining a stiffness of a deposited material by observing changes in the resonance frequency/frequencies or resonance amplitude/s over time.

The apparatus of the above third or fourth aspect of the invention may further comprise a device adapted to give a mechanical impulse to the structure.

DETAILED DESCRIPTION

Figure 1:
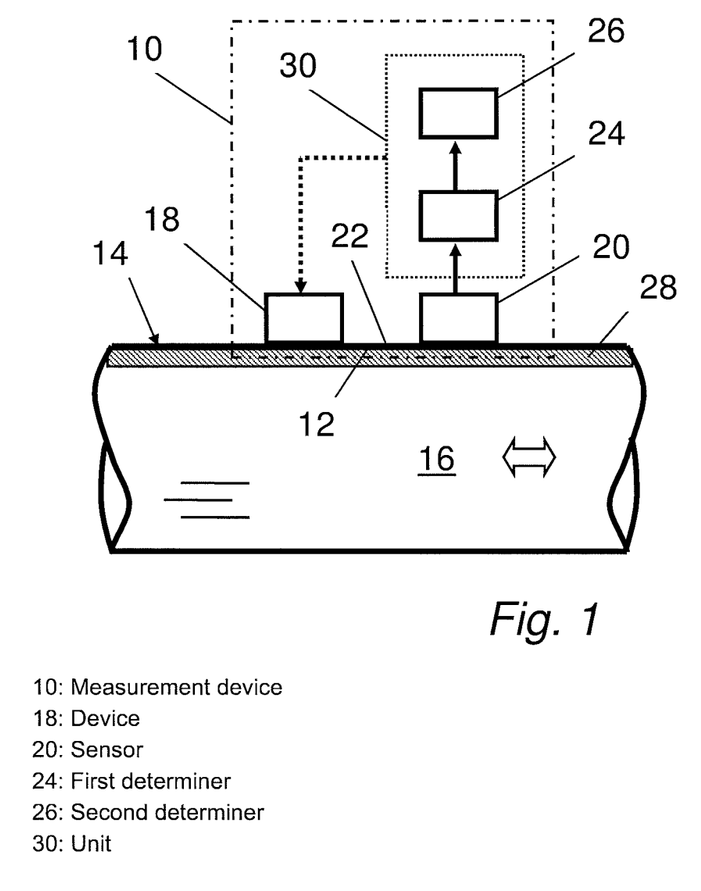
FIG. 1 is a schematic view of a device according to an embodiment of the present invention.

FIG. 1 is a schematic view of a device for measuring the thickness of a deposit of material on an inner wall of a structure according to an embodiment of the present invention. Specifically, the device of FIG. 1. is a measurement device 10 adapted to measure the wax layer thickness on the inside wall 12 of a pipe or pipeline 14 for transportation of oil 16. The pipeline 14 may for instance be made of steel tubes.

The measurement device 10 comprises a device 18 adapted to give a mechanical impulse to the pipeline 14. The device 18 may for example function like a hammer. The device 18 is placeable on the outside of the pipeline 14.

The measurement device 10 further comprises a sensor or detector 20 also placeable on the outside of the pipeline 14. The sensor 20 is adapted to detect vibrations, and convert the vibrations into corresponding electrical energy. To convert vibrations into electrical energy, the sensor 20 may for instance comprise a piezoelectric transducer (not shown).

In use, the device 18 and sensor 20 are both mechanically coupled to an outer surface 22 of the pipeline 14 at a particular portion of the pipeline 14, either directly or through some conveying means (not shown). Further, the generator 18 and sensor 20 are placed next to or near each other, preferably on the same side of the pipeline 14, as illustrated.

The measurement device 10 further comprises a first determiner 24 connected to the sensor 20. The first determiner 24 is adapted to determine a resonance frequency of the pipeline 14 based on vibrations detected by the sensor 20.

The measurement device 10 further comprises a second determiner 26 connected to the first determiner 24. The second determiner 26 is adapted to determine the thickness of any wax layer 28 deposited on the inside 12 of the pipeline 14 based on the resonance frequency determined by the first determiner 24.

Though illustrated as separate elements, the functions of the first and second determiners 24, 26 may be realized by a single unit 30, e.g. a computer device. Such a unit can also be used to control the device 18.

An exemplary operation of the present measurement device 10 will know be described with reference to FIGS. 1-3. At step (a), the device 18 is initially excited so as to give a mechanical impulse to the pipeline 14, causing vibrations in the pipeline. When the pipeline 14 is excited with an impulsive function like the strike by the device 18, the pipeline 14 initially vibrates at all the frequencies present in the impulse (an impulsive function theoretically contains 'all' frequencies). However all frequencies except the eigen frequency and its overtones will be damped quickly, so after a very short time after the impulse, the vibration will consist mainly of the resonant frequencies.

The vibrations generated in the pipeline are then detected by the sensor 20 in step (b). The sensor 20 converts the detected vibrations into corresponding electrical energy, and records the vibration signal over a certain time period.

From the electrical energy representing the vibrations detected by the sensor 20, the first determiner 24 then determines a resonance frequency of the pipeline 14 including any wax deposits in step (c). The first determiner 24 may for instance transform the detected vibrations via FFT (fast Fourier transform) into the frequency domain and plot the output in a x-y (frequency vs. amplitude) type chart, and observe the spike(s) that occur. Each spike is a resonance or resonant frequency of the pipeline 14.

Then, based on the resonance frequency determined by the first determiner 24, the thickness of any wax layer deposited on the inside of the pipeline is determined by the second determiner 26 in step (d). The second determiner 26 may for instance use a x-y (deposit thickness vs. resonance frequency) type chart for the particular portion of the pipeline 14 and input the current resonance frequency (e.g. the first overtone) to determine the current deposit thickness. An example of such a chart is shown in FIG. 3. The chart may be prepared by first using FEM (finite element method) to determine the eigen frequencies of a clean pipeline for the pipeline geometry at the particular portion of the pipeline 14. Then, a layer (deposit) is added inside the clean pipeline, and the eigen frequencies are calculated again. Preferably, these FEM calculations may take into account also the pipeline's surrounding, that means whether the pipeline 14 is suspended in free water, or if it is lying on the sea ground or if it is half-buried in the sea-bed.

The determined thickness may be presented to an operator in a variety of ways (e.g. by means of a display, not shown), as appreciated by the skilled person, and/or be entered into some other system for further processing, etc.

Figure 2:
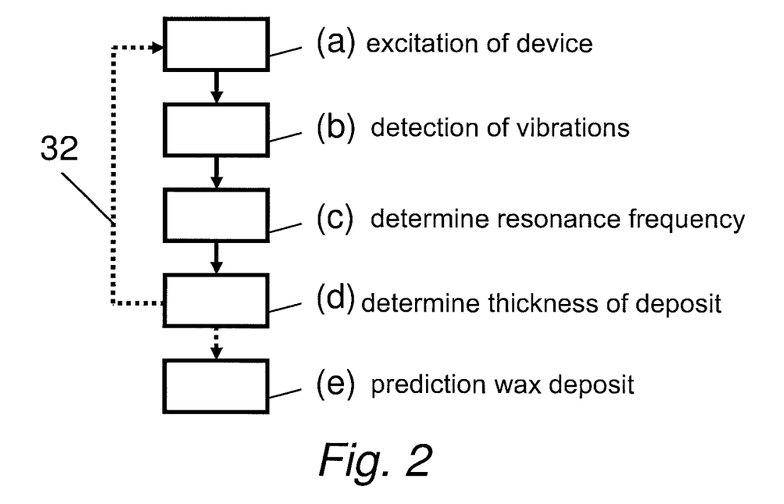
FIG. 2 is a flow chart of a method according to an embodiment of the present invention.
Figure 3:
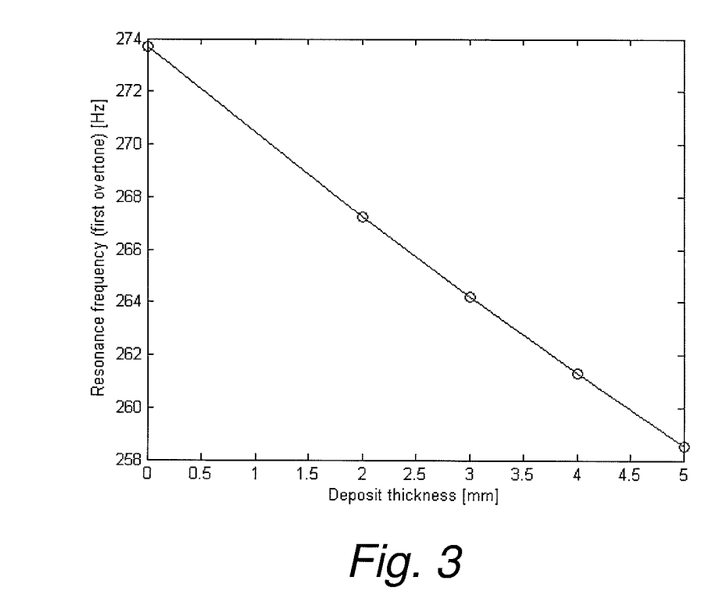
FIG. 3 is an exemplary x-y (deposit thickness vs. resonance frequency) type chart.

Preferably, the above described method is continuously repeated, as indicated by the optional dashed line 32 in FIG. 2, in order to provide a real-time measure of any wax layer deposition thickness.

Figure 4:
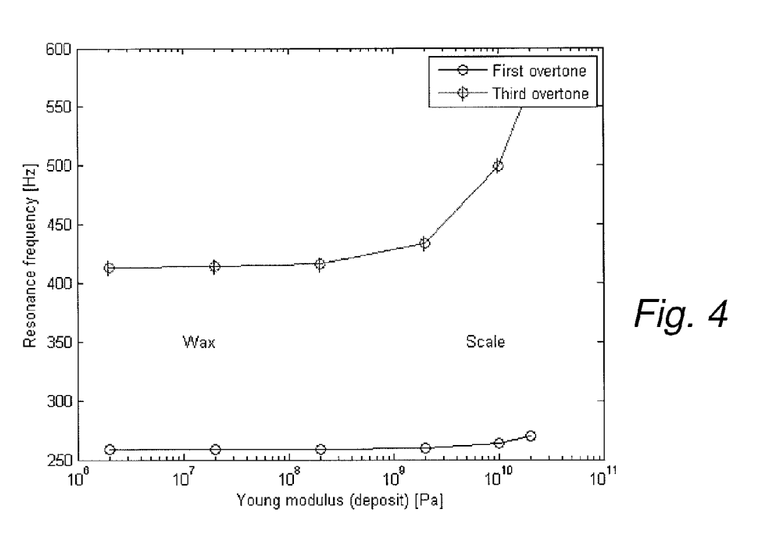
FIG. 4 is an exemplary x-y (Young modulus vs. resonance frequency) type chart.

In a modification of the present device and method, the type of deposition may also be determined, e.g. by means of the second determiner 26. Namely, changing the deposit's Young modulus (i.e. its stiffness) shifts also the eigen frequency, but the shift is different for the different overtones, see FIG. 4. For instance, the shift of the third overtone with respect to stiffness of the deposit is indeed greater than the corresponding shift of e.g. the first overtone. In fact, the first overtone does not vary significantly with respect to the stiffness of the deposit. Therefore, preferably the first overtone, or more preferably the lowest characteristic resonant frequency of the structure, is used to determine the deposit's thickness. On the other hand, the shift in frequency of a higher overtone (e.g. the third overtone) in combination with the determined thickness may preferably be used to determine the Young modulus or hardness of the present deposit. In particular, the shift due to thickness as determined from the first overtone may be deducted from the shift of the third overtone, whereby the hardness of the deposit may be determined from the remaining shift of the third overtone. The hardness may then be used to determine whether the deposit consists mostly of scale which is stiff or wax which is elastic. Charts (like the chart in FIG. 4) may be prepared from FEM by doing calculations for several cases with the same deposit thickness but changing the deposit's elasticity modulus each time.

Further, the first determiner 24 may also be adapted to determine at least one of: (i) the amount of damping of the vibrations at the resonance frequency, i.e. how the amplitude of the resonance frequency decreases over time; (ii) the shift of the frequencies of the harmonics of the structure as the deposition thickness is increased, and (iii) the amount of damping of the vibrations at the harmonics of the structure, based on the detected vibrations. Additionally, the second determiner 26 may also be adapted to determine the elasticity modulus, both the real and the imaginary component, of any deposit of material on the inside of the structure based on data resulting from at least one of (i)-(iii). For instance, the amount of damping for each harmonic frequency will differ depending on the elasticity modulus. To this end, the determiner 26 may utilize a prepared look-up table including different amounts of damping of each harmonic frequency for a given pipeline geometry for a set of elasticity modulus. Based on the currently detected amount of damping of each harmonic frequency, the current elasticity modulus of the deposit may be retrieved. And based on the current elasticity modulus, the kind of deposit may then be determined, at least roughly, like above. For instance, wax is a viscoelastic medium, while scale (precipitated salt) is a comparatively stiff and hard medium. A deposit of equal thickness of these two will show a completely different amount of damping of the vibrations at the harmonics.

Figure 5:
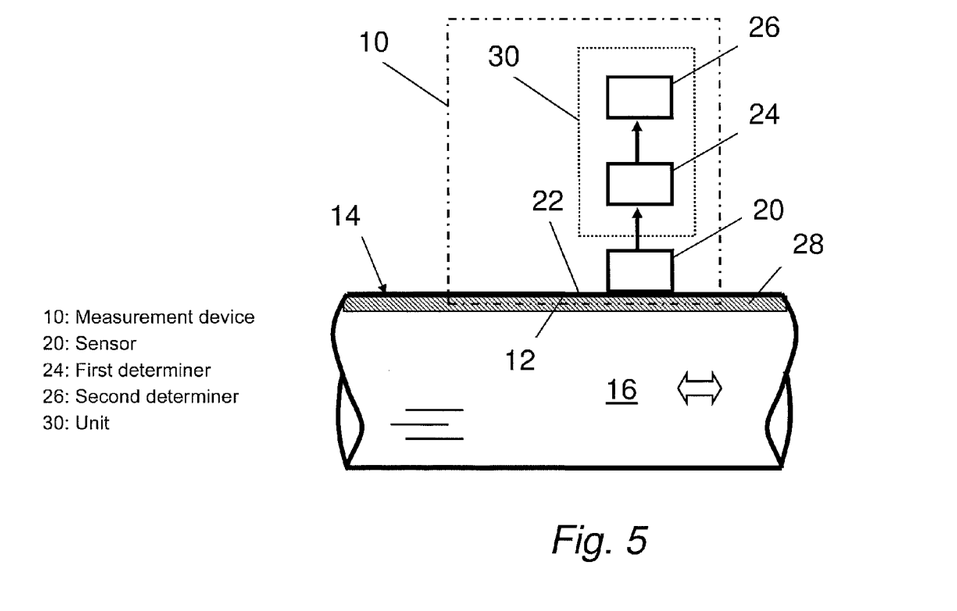
FIG. 5 is a schematic view of a device according to another embodiment of the present invention.

A measurement device according to another embodiment of the present invention as illustrated in FIG. 5 will now be described. The measurement device 10 of FIG. 5 is similar to that of FIG. 1, but the device 18 may be omitted. Instead, the vibrations in the pipeline 14 may be caused by the medium 16 flowing inside the pipeline 14. If the flow is irregular, as in most real production flows, e.g. a two-phase slug flow, it will exchange mechanical energy with the pipe structure 14, setting it into vibration. Alternatively, if the flow is not regular enough, shock waves may be introduced in the flow, e.g. by increasing the flow rate suddenly by a certain percentage. Such shock waves will transverse through the pipeline 14 and introduce vibrations in the pipeline 14 that may be detected.

Basically, the present method using a single measurement device as described above provides a point measurement. However, the exact knowledge of wax thickness at one point makes it possible to adjust in real-time an existing wax deposition model of the pipeline so that a prediction (optional step (e) in FIG. 2) of the wax layer also in a wide distance from the measurement point is possible with very high accuracy. It should generally be sufficient to have a measurement at a few critical points (e.g. tie-in of new wells, junctions, etc.) to cover the complete pipeline. Exemplary wax deposition models that may be used in conjunction with the present invention are disclosed in the publication "Simulating Wax Deposition in Pipelines for Flow Assurance"; Beryl Edmonds, Tony Moorwood, Richard Szczepanski, and Xiaohong Zhang; Energy Fuels, 2008, 22 (2), 729-741.

Figure 6:
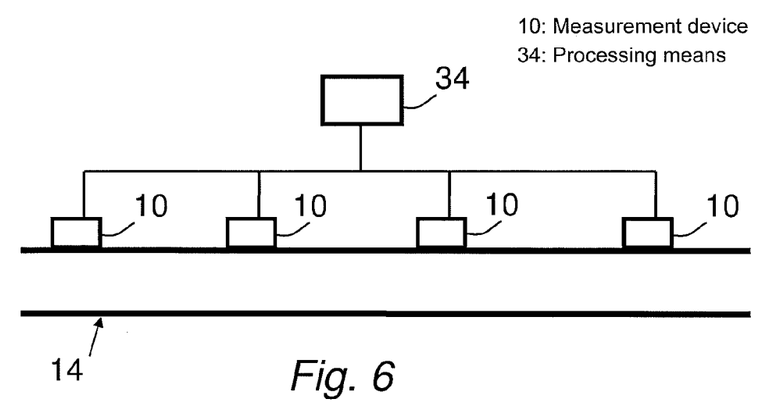
FIG. 6 is a schematic view of an arrangement comprising a pipeline and several measurement devices of the present invention.

Hence, in an advantageous arrangement of the present invention as illustrated in FIG. 6, several measurement devices 10 of the type described above are arranged at different locations along the pipeline 14. Further, a central processing means 34 (e.g. a computer device) is provided, which central processing means 34 is adapted to receive local wax layer thickness data from the measurement devices 10. The received local data may be used by the processing means 34 to predict the wax layer thickness at location remote from where the measurement devices 10 are located, using a wax deposition model of the pipeline 14, as well as to update the present wax deposition model of the pipeline. Certainly, the arrangement of FIG. 6 could also be used without the wax deposition model. In such a case, the output is a plurality of point measurements, one at the position of each measurement device.

Figure 7:
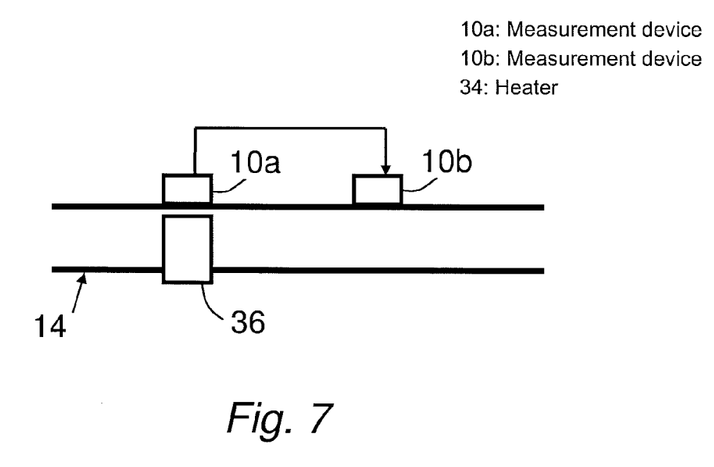
FIG. 7 is a schematic view of an arrangement comprising a pipeline and two measurement devices according to a further embodiment of the present invention.

FIG. 7 is a schematic view of an arrangement according to yet another embodiment of the present invention, wherein two measurement devices 10a, 10b are arranged at different locations along the pipeline 14. The devices 10a, 10b are basically of the same type as the device 10 described above, though the determiners 24 and 26 may be omitted in device 10a.

At the portion of the pipeline 14 where the device 10a is arranged, there is also provided a heater 36. The heater 36 is adapted to heat the inner wall of said portion of the pipeline 14 to a temperature above wax appearance temperature, thus preventing deposition in the heated portion. The heater 36 may for instance be electrical heating cables installed locally around the outside of the pipeline 14. The device 10b is on the other hand arranged at a non-heated portion of the pipeline 14, as illustrated. The device 10a and the heater 36 may be placed upstream or downstream of the device 10b.

Upon operation, the device 10a carries out the above steps (a)-(b) for the heated portion of the pipeline 14. At the same time, the device 10b carries out the above steps (a)-(d) for the non-heated portions, but additionally using data resulting from the operation of device 10a as calibration data. For instance, vibrations detected by the device 10a may be subtracted from the vibrations detected by the device 10b when determining the resonance frequency, optionally already in the time domain before a FFT for determining the dominant frequencies of the vibrations is applied. In this way, the device 10b may determine the deposit thickness taking into account vibrations in the pipeline 14 caused by the flow in the pipeline 14.

Figure 8:
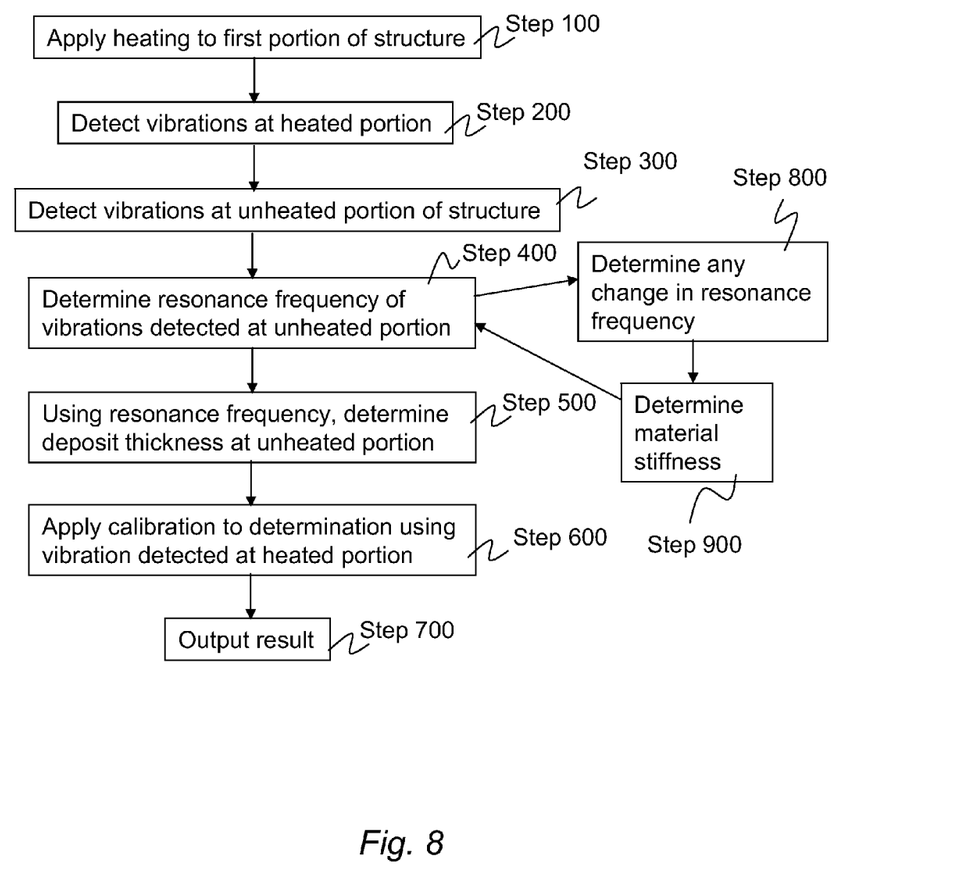
FIG. 8 is a flow diagram illustrating a method of determining the thickness of a deposit and of determining the stiffness of the deposit material.

FIG. 8 illustrates in general terms a method of determining the thickness of a material deposited on an inner surface of a structure such as a pipeline. At step 100, heat is applied to a portion of the structure. At step 200, vibrations are detected at that heated portion. This data provides calibration data indicative of the vibrations present where no deposit exists. At step 300, vibrations are detected at an unheated portion, i.e. at a portion of the structure where a deposit is formed. At step 400, these vibrations are analysed and a resonance frequency (or frequencies) determined. At this stage, changes in the resonance frequency (or frequencies) with time may be monitored, and used to determine a material thickness, steps 800 and 900. Following the determination of the resonance frequency, at step 500, the thickness of the deposit is determined. Using the vibrations detected at step 300, the result is calibrated at step 600. The result is output at step 700.

The person skilled in the art realized that the present invention by no means is limited to the preferred embodiment(s) described above. On the contrary, many modifications and variations are possible within the scope of the appended claims. For instance, the present invention is applicable to all kinds of structures or containers conducting hydrocarbon streams, which hydrocarbon streams comprise components that possibly deposit on the container wall, e.g. wax. Also, in the arrangement of FIG. 6, the first and second determiners 24, 26 of each device 10 may be centralized to the processing means 34. Also, instead of using the sensor 20, the vibrations in the pipeline 14 may be detected by means an optical detector or an accelerometer.

The invention claimed is:

1. A method of measuring the thickness of a deposit of material on an inner wall of a structure, the method comprising:
    (a) heating a portion of the structure;
    (b) detecting vibrations at the heated portion;
    (c) detecting vibrations at an unheated portion of the structure;
    (d) determining a resonance frequency or frequencies of the structure at the unheated portion of the structure based on the vibrations detected at (c); and
    (e) determining the thickness of a deposit of material on the inner wall of the structure at said unheated portion using the determined resonance frequency or frequencies at the unheated portion of the structure, wherein the detected vibrations of step (b) at the heated portion are used for calibrating the detected vibrations at the unheated portion of step (c) before steps (d) and (e) are carried out.

2. The method according to claim 1, and comprising a further step of inducing said vibrations in the structure by means of a device adapted to give a mechanical impulse to the structure.

3. The method according to claim 1, wherein the vibrations in the structure are caused by means of a medium flowing inside the structure.

4. The method according to claim 1, wherein the vibrations in the structure are caused by changing the flow rate of a medium flowing inside the structure.

5. The method according to claim 1, wherein the vibrations in the structure are detected by means of at least one of: a sensor mechanically connected to the structure, an optical detector, and an accelerometer fixed to the outside of the structure.

6. The method according to claim 1, wherein the resonance frequency used to determine the thickness of a deposit of material on the inner wall of the structure is the lowest characteristic frequency of the structure.

7. The method according to claim 1, further comprising predicting the thickness of a deposit of material at one or more portions of the structure remote from where the vibrations are detected using a material deposition model of the structure.

8. The method according to claim 1 and comprising performing the method for different portions of the structure.

9. The method according to claim 1, wherein a resonance frequency of the structure is determined by determining the frequency at which the structure vibrates at a maximum amplitude.

10. The method according to claim 1, wherein the thickness of any deposit of material on the inner wall of the structure is determined by comparing the determined resonance frequency with a previously determined resonance frequency of the structure.

11. The method according to claim 1, wherein said structure is a pipeline.

12. The method according to claim 1, wherein said material is wax.

13. The method according to claim 1, further comprising determining at least one of:
    (i) an amount of damping of vibrations at the resonance frequency;
    (ii) a shift of the frequencies of the harmonics of the structure; and (iii) an amount of damping of the vibrations at the harmonics of the structure, based on the detected vibrations.

14. The method according to claim 13, further comprising determining the elasticity modulus of a deposit of material on the inner wall of the structure based on data resulting from at least one of (i) to (iii).

15. A method of determining the stiffness of a material deposited on an inner wall of a structure, the method comprising:
  detecting vibrations in the structure;
  determining a resonance frequency or frequencies of the structure based upon the detected vibrations; and
  determining a stiffness of a deposited material by observing changes in the resonance frequency/frequencies or resonance amplitude/s over time.

16. An apparatus for measuring the thickness of a deposit of material on an inner wall of a structure, the apparatus comprising:
  a heater configured to heat a first portion of the structure;
  at least one sensor placeable on the outside of the first portion of the structure or on the outside of a second portion of the structure for detecting vibrations in the first portion of the structure and the second portion of the structure, wherein the second portion of the structure is unheated;
  a signal processor configured to determine a resonance frequency of the structure at the second portion of the structure based on the vibrations detected by the at least one sensor at the first portion of the structure and at the second portion of the structure, wherein the vibrations detected at the first portion of the structure are used for calibrating the vibrations detected at the second portion of the structure before said resonance frequency is determined; and
  an analyser configured to determine the thickness of a deposit of material on the inner wall of the second portion of the structure based on the resonance frequency determined by said signal processor.

17. The apparatus according to claim 16, wherein the structure comprises a pipeline.

18. The apparatus according to claim 16, further comprising a device adapted to give a mechanical impulse to the structure.

19. An apparatus for determining the stiffness of a material deposited on an inner wall of a structure, the apparatus comprising:
  a sensor for detecting vibrations in the structure;
  a signal processor for determining a resonance frequency or frequencies of the structure based upon the detected vibrations; and
  an analyser for determining a stiffness of a deposited material by observing changes in the resonance frequency/frequencies or resonance amplitude/s over time.

* * * * *